United States Patent [19]

Fowler et al.

[11] Patent Number: 4,537,484

[45] Date of Patent: Aug. 27, 1985

[54] FINGERPRINT IMAGING APPARATUS

[75] Inventors: Randall C. Fowler, Los Altos, Calif.; Kenneth Ruby, Florence; Thomas F. Sartor, Jr., Eugene, both of Oreg.

[73] Assignee: Identix Incorporated, Palo Alto, Calif.

[21] Appl. No.: 575,842

[22] Filed: Jan. 30, 1984

[51] Int. Cl.³ .............................................. G03B 29/00
[52] U.S. Cl. ........................................... 354/62; 382/4
[58] Field of Search ...................... 354/62, 79, 80, 150, 354/354; 382/4

[56] References Cited

U.S. PATENT DOCUMENTS 3,529,520 9/1970 Thiebault .............................. 354/62
3,975,711 8/1976 McMahon .............................. 382/4
4,152,056 5/1979 Fowler ................................... 354/62

Primary Examiner—L. T. Hix
Assistant Examiner—David M. Gray
Attorney, Agent, or Firm—Limbach, Limbach & Sutton

[57] ABSTRACT

A fingerprint imaging apparatus for use in an identity verification system or the like. The imaging apparatus includes a carriage rotatably mounted on a frame, with the carriage being driven by a stepper motor. A transparent optical element having an arcuate recess for receiving a finger to be imaged is secured to the frame. The rotatable carriage supports a light source and mirror which are positioned adjacent the optical element. The mirror is positioned with respect to the source and optical element to receive light issuing from the element which originated from the source. The light is reflected by the mirror through a lens arrangement to a second mirror and then to a linear photo-diode array which are also mounted on the carriage. When a finger is positioned in the recess of the optical element, the motor causes the carriage to rotate so that the finger is scanned by the light source. The linear diode-array is periodically read out during the scan with the output of the array containing imaging data. The data is then processed as required to accomplish the identity verification function or the like.

9 Claims, 10 Drawing Figures

FINGERPRINT IMAGING APPARATUS

DESCRIPTION

1. Technical Field

The present invention relates generally to imaging apparatus and more particularly to fingerprint imaging apparatus.

2. Background Art

Fingerprint imaging apparatus is presently used for, among other things, recording fingerprints without the use of ink. An exemplary fingerprint imaging apparatus is disclosed in U.S. Pat. No. 4,152,056 entitled "Fingerprinting Arrangement." The apparatus includes a transparent cylinder for receiving a finger from which a fingerprint is to be taken. A platform surrounding the cylinder is provided which carries a light source directed towards the cylinder. The platform is rotated around the cylinder so that the finger is scanned with light. The light reflected from the cylinder and the finger disposed therein contains information relating to the skin ridge patterns which is recorded by a camera moving with the light source.

Although the above-described imaging apparatus constituted an improvement in the art, shortcomings remain. By way of example, the prior art apparatus is difficult to implement in a compact form. In addition, a mechanism must be provided for rotating the camera with respect to the light source so that an image is laid over the surface of the camera film. As will become apparent to a person skilled in the art upon reading the following Best Mode for Carrying Out the Invention, together with the drawings, the present invention overcomes the above-noted and other limitations of the prior art imaging apparatus.

DISCLOSURE OF THE INVENTION

A fingerprint imaging apparatus is disclosed. The apparatus includes a rigid frame with a carriage rotatably mounted on the frame. A transparent optical element for receiving a finger to be imaged is secured to the frame. The optical element is preferably made of plastic and has a partial cylindrical cross-section which provides a recess for receiving the finger.

The rotatable carriage is driven by a motor, preferably an electric stepper motor. The carriage supports a light source and a light detector which typically includes a pair of mirrors, a lens assembly and a light sensitive element such as a photo-diode array. The light detector is positioned on the carriage to receive light from the optical element which originated from the light source. The position of the light detector remains fixed with respect to the light source.

In the prefered embodiment, one of the mirrors of the light detector is positioned on an elongated carriage member adjacent the optical element. The light source is secured to a second elongated carriage member, also adjacent the optical element, with the relative radial positions of the source and mirror being adjusted so that light originating from the source which is transmitted from the optical element is received by the first mirror. The second mirror receives the light from the first mirror through the lens assembly and transmits the light to the photo-diode array.

The carriage is rotatably driven by the motor such that at least a substantial portion of the finger is scanned by the light source. The light issuing from the optical element contains fingerprint image information which is received by the diode array. The data output of the array may then be processed as required to perform various functions such as identity verification.

BEST MODE FOR CARRYING OUT THE INVENTION

Figure 1:
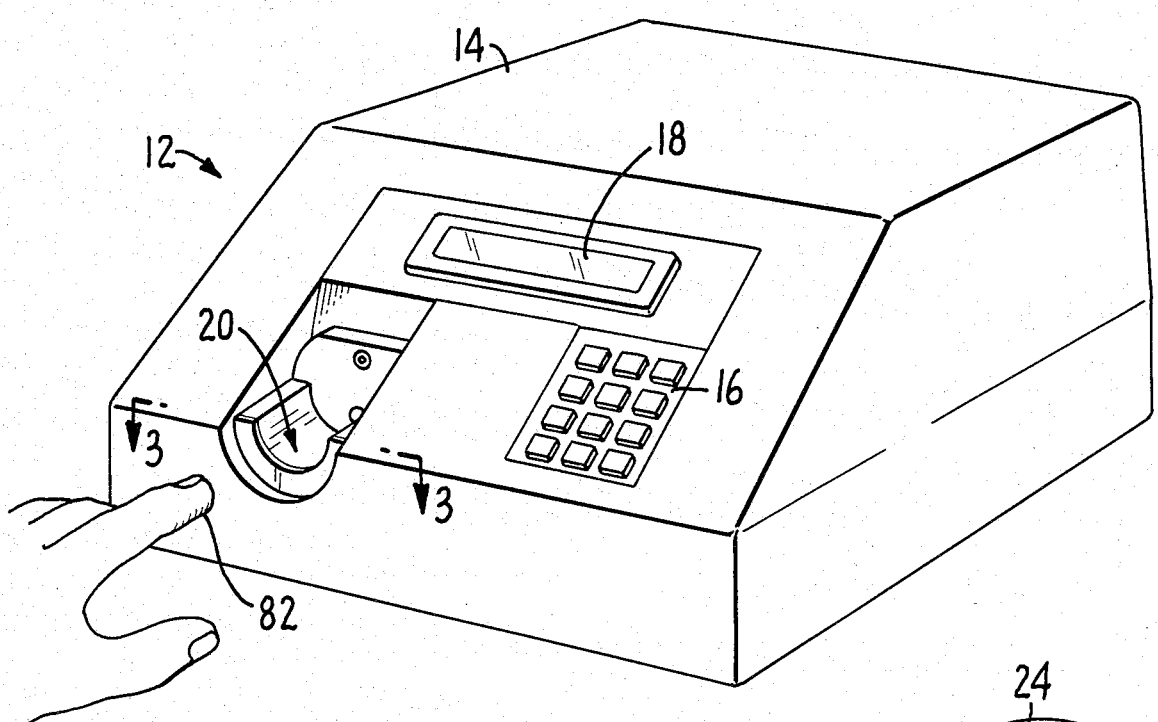
FIG. 1 is a perspective view of a fingerprint verification terminal which utilized a fingerprint imaging apparatus in accordance with the present invention.

Refering now to the drawings, FIG. 1 shows an exemplary application of the subject fingerprinting imaging apparatus in a fingerprint verification terminal, generally designated by the numeral 12. One or more of such verification terminals, in conjunction with a host computer (not shown), are typically used to control the access of individuals to facilities or computers.

Terminal 12 includes a housing 14 which encloses the subject imaging apparatus. Housing 14 has an inclined front panel (not designated) on which a keyboard 16 and a display 18 are mounted. The front panel further includes a recess in which an optical element 20 of the subject imaging apparatus is mounted.

Terminal 12 is used both for verification and enrollment. In both instances, the individual to be either enrolled or verified places a finger 82 or thumb in the recess defined by optical element 20. Sensing circuitry detects the presence of the digit on the element which causes a series of prompting messages to be shown on display 18. If the individual has been previously enrolled, the individual is requested to enter his/her personal identification number, name, or other form of identification. The finger is then scanned utilizing the subject imaging apparatus to provide an image which corresponds to the individual's fingerprint. Next, a comparison between the image and a stored image for the individual is performed. If the comparison is positive, the individual is given physical access to the facility or data access.

The enrollment procedure is similar to the verification procedure in that the individual's finger is scanned and data corresponding to the fingerprint image is stored in a non-volatile memory. Also, identification information, such as the individual's name or personal identification number, is stored using keyboard 16. Security personnel are typically present during the enrollment procedure to verify the individual's identity. Once the individual has been enrolled, physical access or data access may be obtained by the individual utilizing the previously-described verification procedure, such procedure not requiring the presence of security personnel.

Figure 2:
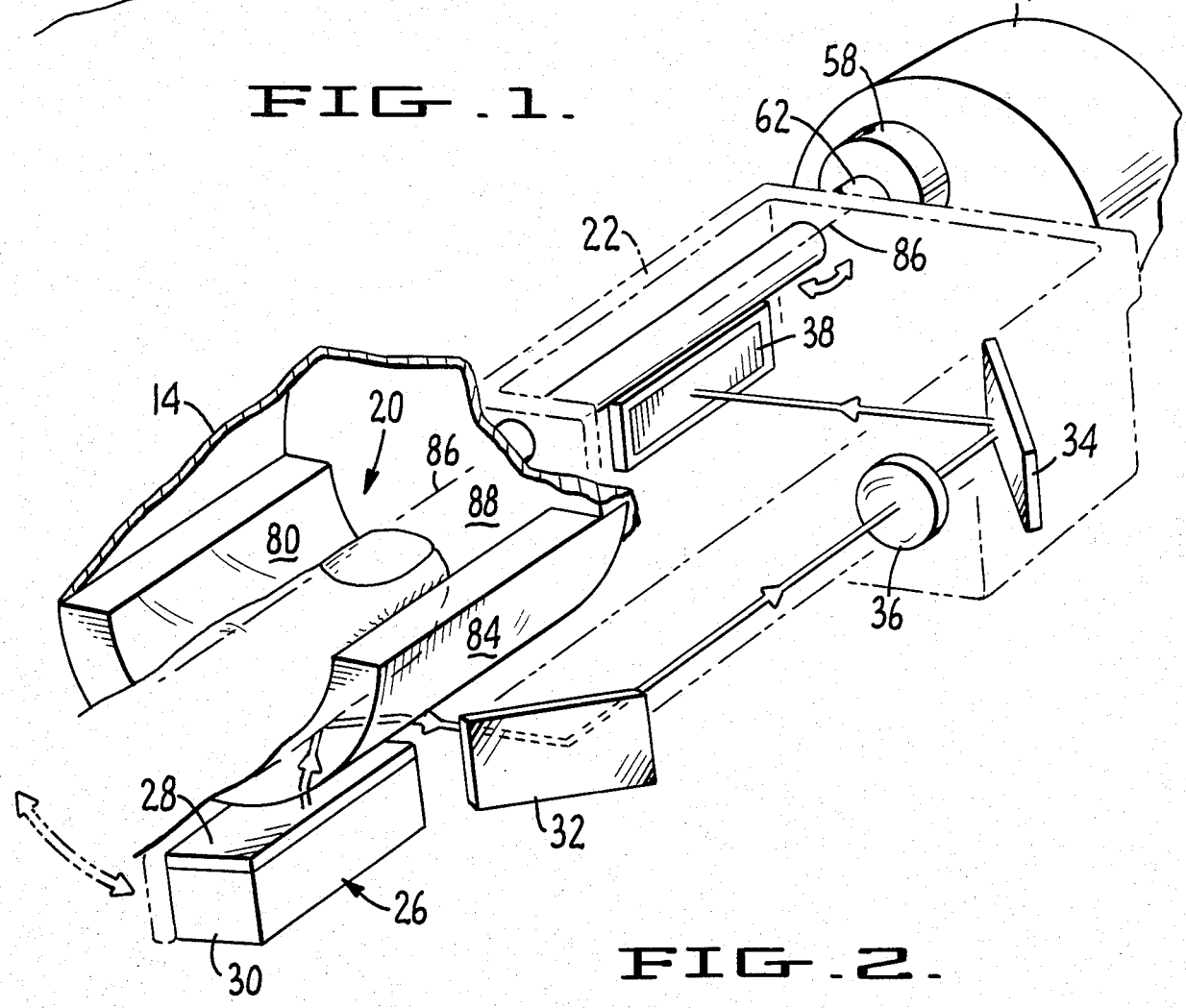
FIG. 2 is a schematic drawing of an imaging apparatus in accordance with the present invention showing the relative postion of some of the primary components of the apparatus.

Some of the details of the construction of the subject imaging apparatus may be seen in FIG. 2. Optical element 20 is fabricated from a transparent material, such as acrylic plastic, having a known index of refraction. The body of element 20 is in the form of cylinder having a longitudinal or primary axis 86. A half-section of the cylinder defined by a bisecting plane which lies on axis 86 is removed to form a recess for receiving finger 82. As can best be seen in FIG. 8, the inner surface 80 of element 20 defines an arcuate section having a constant radius $R_I$ with respect to axis 86. Similarly, the outer surface 84 of the element defines a second arcuate section having a constant radius $R_O$ with respect to axis 86. Radii $R_O$ and $R_I$ are typically approximately 1.0 and 0.6 inches, respectively.

Optical element 20 further includes a mounting section 88, generally transverse to axis 86, which is an integral part of the main half cylinder section. Mounting section 88 is located at the far end of element 20 and is used to rigidly secure the element to the frame of the subject apparatus. Mounting section 88 could also be in the form of a disc which is secured to the main body section. In that event, the main body section could be fabricated from a plastic cylinder. Prior to mounting the disc on the main body, the inner and outer surfaces 80 and 84 can be readily polished.

The imaging apparatus further includes a carriage 22 which is rotatable about axis 86. Carriage 22 carries an elongated light source, generally designated by the numeral 26. The carriage also supports first and second mirrors 32 and 34, respectively, a lens assembly 36 and a linear photo-diode array 38. Carriage 22 is rotated about axis 86 by a stepper motor 24, as will be described subsequently.

Light source 26, which is positioned adjacent surface 84 of the optical element, has a principle axis which is parallel with axis 86. Light source 26 includes a base 30 which is typically one and one-half inches in length and a translucent light diffuser 28 which is secured to the base. An array of small incadescent bulbs is mounted in base 30 so as to provide a relatively uniform diffused source of light along the length of the base.

Mirror 32 is a first surface-type mirror wherein the reflecting surface is disposed on the outer surface of the mirror. Mirror 32 is at a 45° angle with respect to light source 26 so as to receive light reflected from optical element 20, as will subsequently be described.

Photo-diode array 38 is secured on carriage 22 with the major axis of the linear array being parallel with respect to axis 86. Second mirror 34, which is also a first surface-type mirror, is positioned on carriage 22 to receive light through the lens assembly 36 from mirror 32 and reflect it to the surface of array 38. Thus, mirrors 32 and 34 have the same radial position with respect to axis 86, with the longitudinal axis of mirror 34 being 45° with respect to axis 86. Photo-diode array 38 includes a linear array of 512 photo-diodes spaces on 0.001 inch centers to form an array approximately 0.50 inches in length. The diodes and associated circuitry are preferably assembled in a single package. An array marketed by EG&G Reticon of Sunnyvale, Calif. under the designation "RL512G" has been found suitable for the present application. Other types of photosensitive devices could be used for this purpose.

Lens assembly 36, which is secured on carriage 22 between mirrors 32 and 34, may include a single lens, as depicted, or a plurality of lenses. Lens assembly 36 is configured to focus light originating from surface 80 of the optical element onto the surface of diode array 38. Assembly 36 also serves to de-magnify the image reflected by mirror 32 so that the approximately one inch image at surface 80 is reduced to a one-half inch image on the surface of photo-diode array 38 to conform to the length of the array.

Refering now to FIGS. 3 through 7, further details of the construction of an exemplary embodiment of the subject imaging apparatus may be seen. The apparatus includes a rigid metal frame 40, as can best be seen in FIG. 4, which is secured to a base plate 60 on three vertical legs 42 by way of screws. Frame 40 includes downward projecting vertical forward and rear sections (not designated) connected together by a horizontal plate, with legs 42 being connected to the plate. Preferably, frame 40 is machined from a single aluminum casting to form an integral unit, although other materials may be used.

Figure 5:
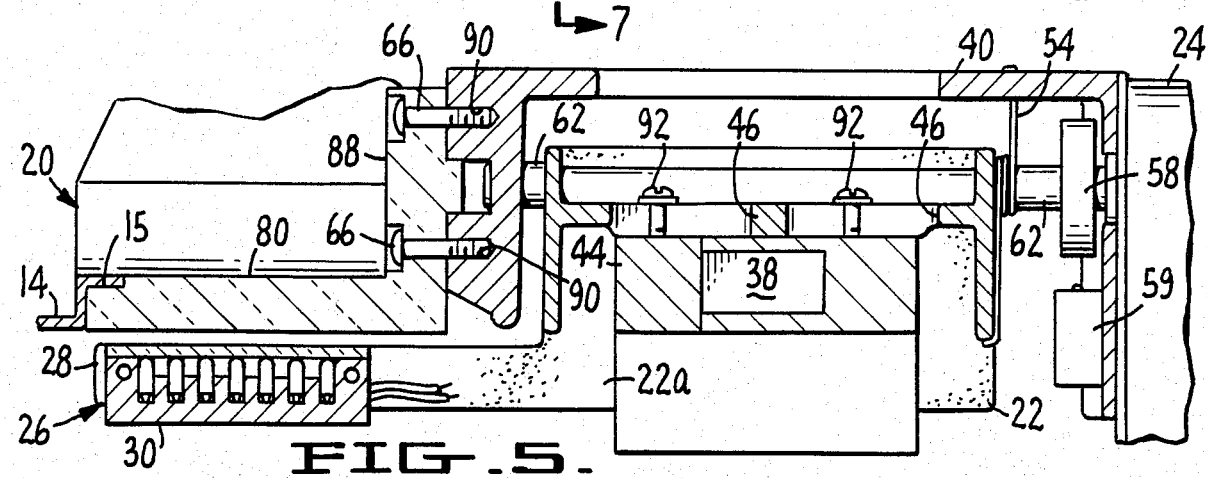
FIG. 5 is a cross-sectional side elevational view of the subject imaging apparatus taken through section line 5—5 of FIG. 3.

Optical element 20 is rigidly secured to the vertical forward section of frame 40 by way of a pair of screws 66 (FIG. 5). Screws 66 extend through counter-sunk bores (not designated) located in the mounting section 88 of the element and into corresponding threaded bores 90 located in the vertical front section of frame 40. Optical element 20 is positioned on frame 40 such that the longitudinal axis of the element is coaxial with the primary axis 86 of the frame. Optical element 20 preferably includes a cutout 15 in the forward portion thereof (FIG. 5) to receive a corresponding flange formed in housing 14 so as to effect a seal.

Figure 3:
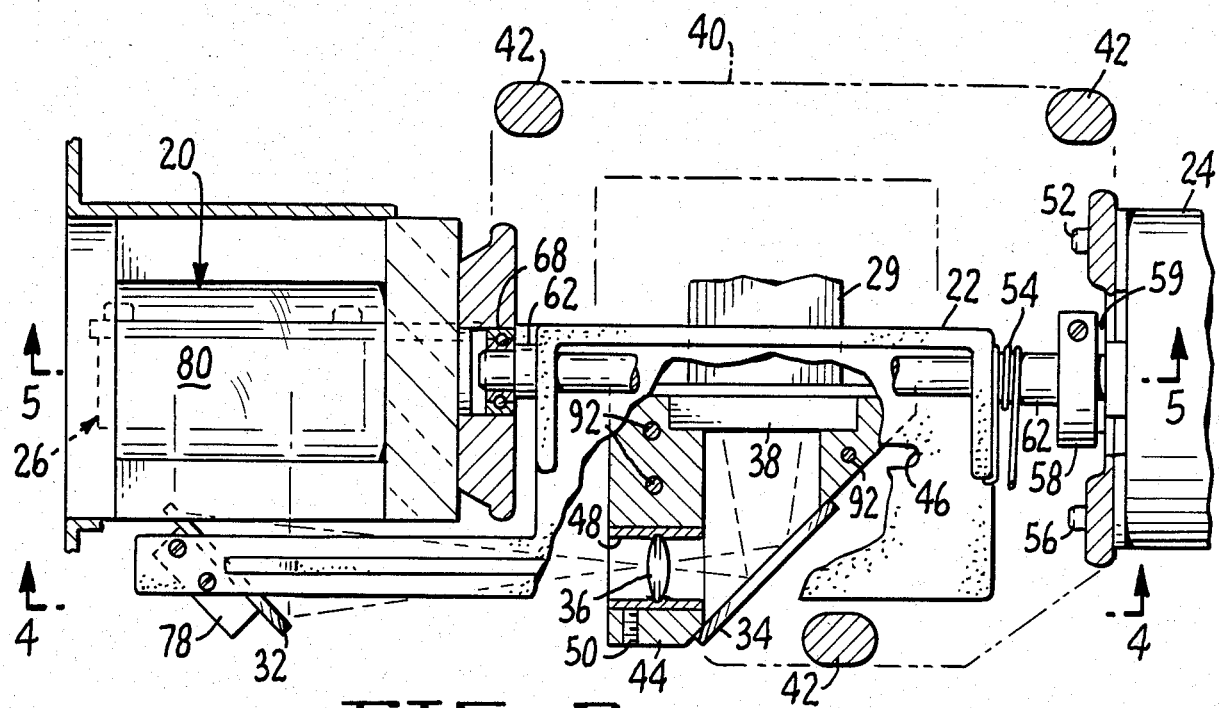
FIG. 3 is cross-sectional plan view of the subject imaging apparatus taken through section line 3—3 of FIG. 1.
Figure 4:
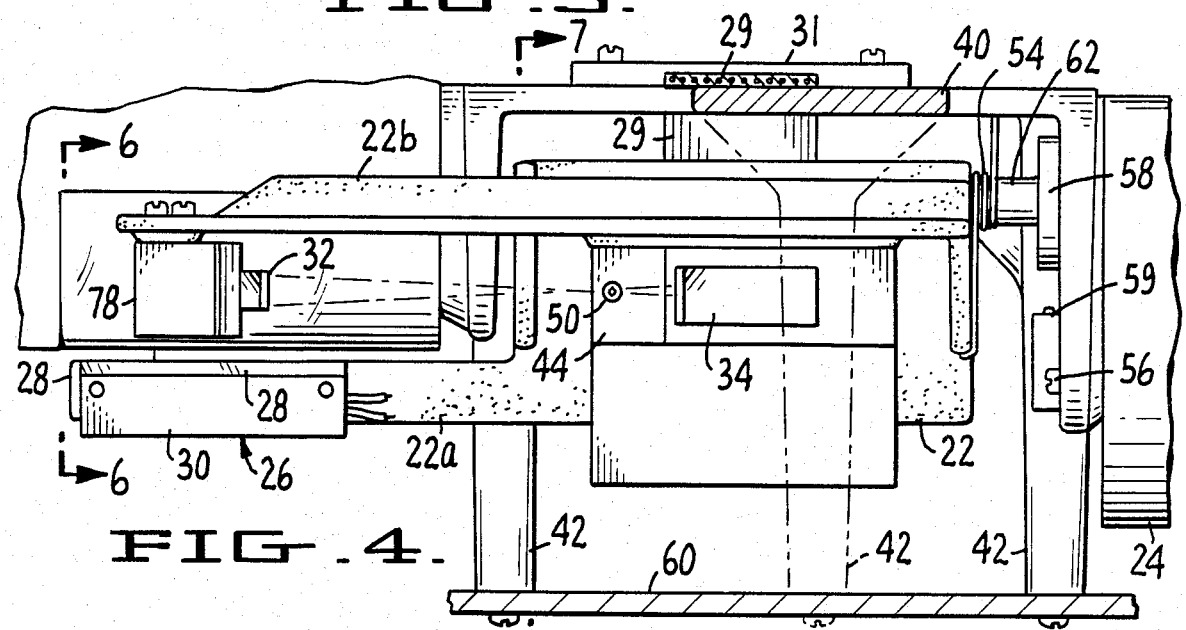
FIG. 4 is a cross-sectional side elevational view of the subject imaging apparatus taken through section line 4—4 of FIG. 3.

Stepper motor 24 is rigidly secured to the vertical back section of frame 40 by a pair of screws 52. The drive shaft of motor 24, which extends through an opening in the back frame section, is coaxial with primary axis 86. Rotatable carriage 22 is hung below the top plate of frame 40 between the front and rear vertical sections. Carriage 22 is provided with a longitudinal bore which receives a mounting shaft 62 (FIG. 3). Shaft 62 is rigidly secured to carriage 22 by a locking pin (not shown) which extends through the carriage and into the shaft. The forward end of shaft 62 is mounted in a bore in the front vertical frame section on bearing 68. The rear end of shaft 62, which is coaxial with axis 86, is connected to the drive shaft of motor 24 by way of a clamp 58. A tensioning spring 54 extends around mounting shaft 62, with one end of spring 54 being secured to carriage 22 and the remaining end being positioned against the horizontal plate of frame 40 (FIG. 4). Spring 54 provides a tension force to carriage 22 which eliminates backlash caused by the internal stepper motor 24 gear train.

Carriage 22 includes a pair of elongated mounting members 22a and 22b which extend below the forward section of frame 40 and which are both generally parallel with primary axis 86. Mounting member 22b (FIG. 4) has a T cross-section and serves to support mirror 32 adjacent optical element 20. A mounting member 78 is provided for securing the mirror to the elongated member. Elongated member 22a is used to support light source 26 adjacent to the optical element. As can perhaps best be seen in FIG. 6, light source 26 and mirror 32 supported by the elongated members of the carriage are radially spaced apart with respect to the primary axis by approximately 45°.

A mounting block 44, which is fastened to the underside of rotating carriage 22, carries lens assembly 36, mirror 34, and photo-diode array 38. Block 44 is secured to carriage 22 by three screws 92 which extend through elongated openings 46 (FIGS. 3 and 5) in the carriage. The openings are parallel with primary axis 86 so that the longitudinal position of the block along axis 86 may be changed by loosening screws 92, repositioning block 44 and retightening the screws.

As can best be seen in FIG. 3, block 44 is provided with a bore which receives a lens assembly mounting cylinder 48 in which lens assemby 36 is mounted. Cylinder 48 is slideably mounted within the bore and is secured in place by a set screw 50. Block 44 also supports mirror 34 at a 45° angle with respect to axis 86. In addition, photo-diode array 38 is secured to block 44 with the array plane being parallel with the primary axis.

The length of the optical path between photo-diode array 38 and lens 36 is adjusted by loosening set screw 50 and sliding cylinder 48 within the mounting block bore. The length of the optical path between the lens assembly and surface 80 of optical element 20 is adjusted by using screws 92 to change the position of mounting block 44 on carriage 22. As previously noted, the two optical paths are adjusted so that the image on surface 80 is focused on the array. In addition, the paths are selected to provide the desired two-to-one reduction.

Electrical connection between the rotating light source and photo-diode array and the non-rotating components is accomplished by way of a flexible flat cable 29. One end of cable 29 is secured to rotating block 44 with the remaining end being secured to the top plate of frame 40 by a clamp assembly 31 (FIG. 4). A loop is formed in the cable between the frame and carriage so that the cable is not stressed when the carriage is rotated.

Figure 8:
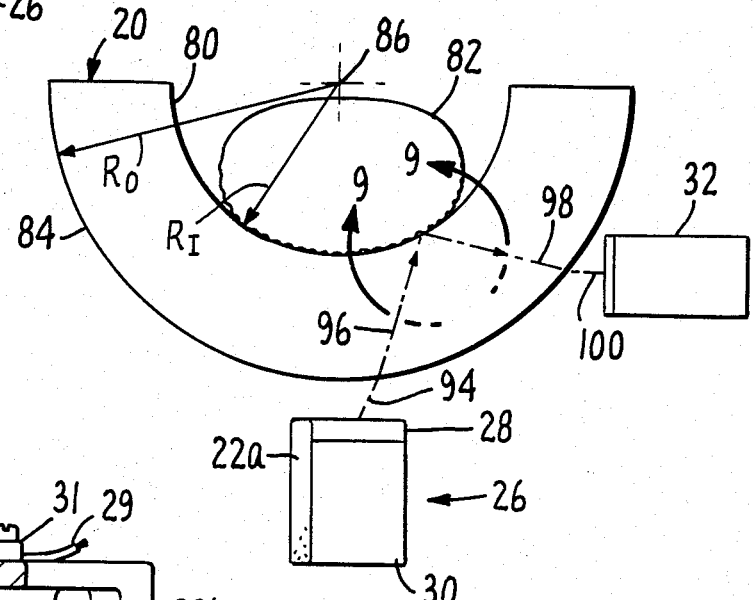
FIG. 8 is a schematic illustration of an exemplary light path through the optical element of the subject imaging apparatus.
Figure 7:
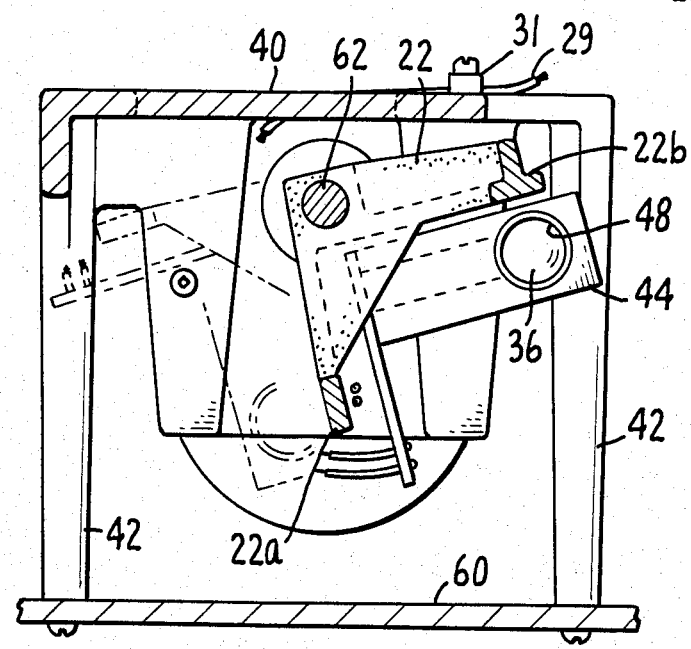
FIG. 7 is a cross-sectional front view of the subject imaging apparatus taken through section line 7—7 of FIG. 4.
Figure 9:
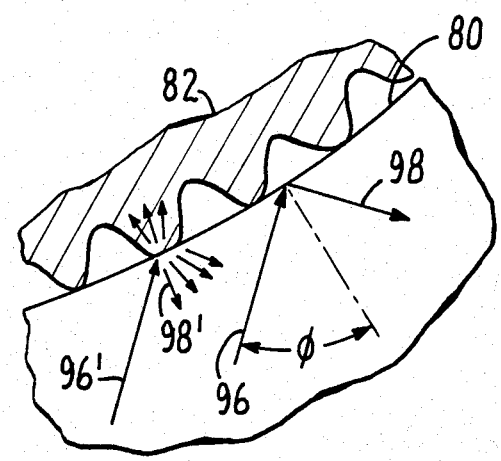
FIG. 9 is an enlarged portion of a section of the schematic illustration of FIG. 8.

Refering now to FIGS. 8 and 9, exemplary light paths through optical element 20 are illustrated. Light source 26 is shown at a typical position during the imaging scan. Line 94 represents an exemplary light ray emitted from source 26 which extends down the length of optical element 20, along primary axis 86, for approximately one inch. As the ray enters the optical element at surface 84, the light is refracted. The amount of refraction, according to well-known laws of optics, is a function of the index of refraction of the optical element medium and the angle of incidence of the ray.

The light ray will continue through the optical element until it reaches surface 80 of the element as represented by line 96. As shown in FIG. 9, at surface 80 ray 96 strikes a portion of the element 20 intermediate two adjacent skin ridges of finger 82. The angle of light source 26 and surface 80 is maintained at a constant value throughout the image scan so that the angle of incidence $\phi$ at surface 80 remains constant. There is a critical angle of incidence where all light is reflected from surface 80 back through the optical element. When the medium opposite the surface is air, the critical angle is typically approximately 45°. Angle $\phi$ is set to a value which is somewhat greater than the critical angle so the light striking surface 80 between skin ridges will be reflected, as represented by line 98.

As shown in FIG. 8, reflected light ray 98 will be transmitted through the optical element until it reaches outer surface 84 of the element. As indicated by line 100, the ray will then be received and reflected by mirror 32 to the diode array.

Refering again to FIG. 9, line 96' represents a light ray which was produced somewhat earlier during the image scan. Ray 96' strikes a skin ridge at angle $\phi$, such ridge having an index of refraction considerably greater than air. Because of the increase of the index of refraction, the total internal reflection is frustrated and most of the incident light is absorbed in finger 82. Some of the incident light is also reflected by the ridge and is dispersed in several directions as represented by lines 98'. Although some of the reflected light reaches diode array 38, the intensity of the light is significantly less than light reflected from surface 80 in regions adjacent the valleys located between the ridges.

The subject imaging apparatus further includes a carriage home position detector 59 which is secured to the rear vertical section of frame 40 immediately below clamp 58. Detector 59 includes a light source (not shown) which directs light towards clamp 58 and a photo-detector (not shown) which receives light reflected from the clamp. The clamp is provided with adjacent reflective and non-reflective surfaces with the juncture of the surfaces being located immediately above detector 59 when the carriage is rotated to the home position, as will be subsequently described. Thus, the output of the photo-detector will change abruptly when the carriage reaches the home position.

Figure 10:
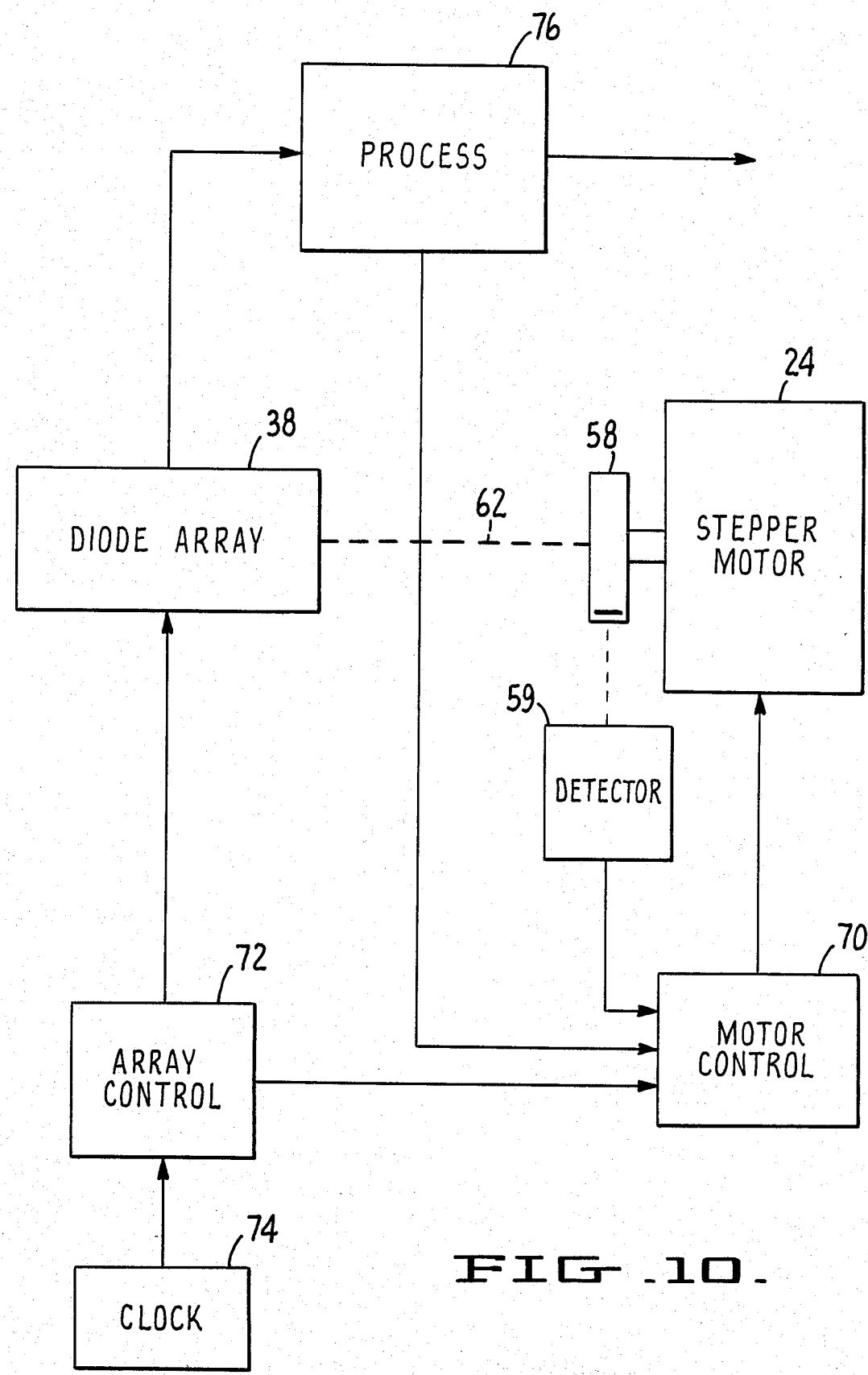
FIG. 10 is a simplified block diagram of an exemplary electrical control system for the subject imaging apparatus.

Refering now to FIG. 10, stepper motor 24 is driven by a motor control as represented by block 70. The motor control produces conventional drive pulses which causes motor 24 to advance in either direction at controllable rates. The rate of drive is a function of the frequency of the pulses and the internal stepper motor gearing arrangement.

Diode array 38 is controlled by array control circuitry, represented by block 72, which receives clock signals from a clock represented by block 74. Array control 72 provides the various conventional control signals to the array including clock signals, refresh signals, and recharge signals. The clock signals cause serial data associated with each diode of the array to be transferred to process circuitry as represented by block 76. The start signals are produced typically every 6 milliseconds, a time consistent with the time required to read out data for each of the 512 diodes in the array. The start signal is also used by motor control 70 to drive stepper motor 24.

Figure 6:
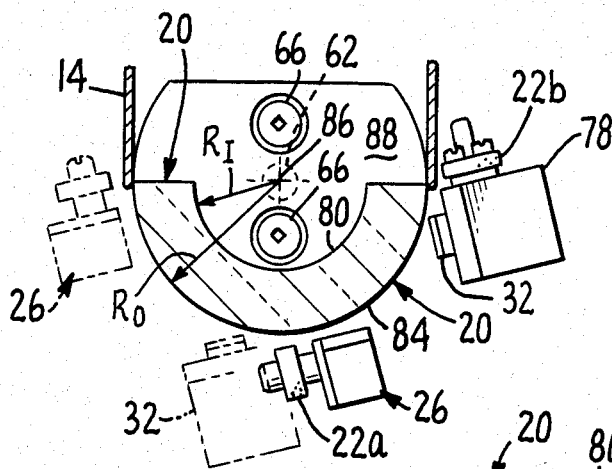
FIG. 6 is a front view of the optical element for receiving a finger together with the associated light source and mirror, taken from line 6—6 of FIG. 4.

FIG. 6 illustrates two exemplary positions of light source 26 and mirror 32. The solid line drawings represent the position of the light source and mirror at the end of the scan. The location of the source and mirror at the beginning of the scan are shown in phantom lines. Prior to the initiation of the scan sequence, light source 26 is located at the home position (not depicted) intermediate the scan start and scan stop positions where incident ray 96 strikes generally the central portion of surface 80 of the optical element. When a finger is not present in the optical element, substantially all of the light will be reflected to mirror 32 along the entire length of the element. Thus, each diode of the linear diode array will receive the maximum amount of light.

The contents of the array are periodically read out and are transferred to process unit 76 which determines that all diodes are illuminated, thereby indicating that a finger is not positioned in the optical element.

When a finger is positioned on optical element 20, the skin ridges of the finger will cause at least some of the light to be absorbed or diffused as indicated by light rays 98' of FIG. 9. At least some of the diodes will no longer receive the maximum amount of light. When the diode array is read out, process unit 76 will detect that a finger is present and will either command motor control 70 to begin an imaging sequence or will cause a promoting message to be shown on display 18.

Motor control 70 will then provide stepper motor 24 with step pulses derived from the start signals produced by array control 72. The step pulses will cause carriage 22 to be driven in a clockwise direction towards the scan start position as shown in phantom in FIG. 6. At the scan start position, light from the source 26 is incident at a point on inner surface 80 of the optical element approximately 45° from vertical. During the movement of the carriage from the home position to the scan start position, data read from array 38 is disregarded.

Motor control 70 then causes motor 24 to drive carriage 22 in a counterclockwise direction to effect a scan. The motor is stepped once every 6 milliseconds so that the entire contents of photo-diode array 38 can be read out once every step. The data from the array is then either stored in a memory for later processing or is processed in real times by process unit 76, as required. The carriage is advanced in the counterclockwise direction until the carriage reaches the scan stop position where the light from source 26 strikes the inner surface 80 of the optical element at approximately 45° from vertical, as shown in solid lines in FIG. 6. Thus, the total scan angle is approximately 90°. Motor control 70 then causes the carriage to be driven back towards the home position. When the carriage reaches the home position, detector 59 commands motor control 70 to stop the motor, thereby terminating the imaging sequence. The data read from diode array 38 is processed, as required, to complete a verification or enrollment procedure.

Linear diode array 32 has 512 diodes which sample light along the longitudinal axis of the optical element. Since the length of image is approximately one inch, data is provided for producing pixels spaced apart along the longitudinal axis approximately 0.002 inches. This provides more than adequate resolution since the skin ridges are typically spaced 0.020 inches apart. In order to provide approximately the same resolution in the perpendicular axis, each step of motor 24 should cause the incident light beam 96 to advance approximately 0.002 inches along inner surface 80 of the optical element. The magnitude of the advance is a function of the angular rotation of motor 24 per step and the inner radius $R_I$ of the optical element. Since there are only a limited number of gear ratios available for motor 24, it is usually preferable to select a ratio which approximately achieves the desired lineal advance and then to adjust radius $R_I$ to provide the final value. Given a typical radius $R_I$ of 0.060 inches and a typical scan angle of 90°, there will be roughly 450 motor steps for each imaging scan. Thus, imaging data will be provided to produce a 512 by 450 pixel map. Each pixel has one bit of resolution (black/white), although greater resolution could be provided if desired to provide a gray scale.

Mirror 32 is preferably radially disposed about axis 86 to receive light reflected off of surface 80 in the region intermediate the skin ridges, as indicated in FIGS. 8 and 9. However, it would be possible to alter the relative radial positions of light source 26 and mirror 32 so that light reflected off surface 80 in the region between the skin ridges does not strike the mirror. Thus, when a valley is scanned, the photo-diode array receives a minimum amount of light. When a skin ridge is scanned, the array receives light which is reflected and diffused by the finger in several directions as represented by rays 98' of FIG. 9. The image produced would be the negative image of that produced utilizing the preferred approach. In addition, the difference in light intensity between a ridge and a valley using the alternative approach would be less than using the preferred approach, therefore the signal-to-noise ratio would be somewhat inferior.

It should also be noted that the area of the finger scanned could also be altered provided sufficient data is acquired to produce a reliable indentification. For example, the 90° scan angle could be reduced or increased somewhat. In addition, certain dimensions of optical element 20, including the thickness $(R_0 - R_I)$ of the element, could be altered without seriously reducing the effectiveness of the subject imaging apparatus. Although the main body of element 20 is in the form of a half cylinder, the body could be something greater or less than a half cylinder. It is preferable that the angle spanned by surfaces 80 and 84 of the optical element be at least 60° to insure that a sufficient portion of the finger is scanned. In addition, the minimum angle provides a recess in the element of sufficient depth so that the finger will be automatically guided to the desired position on the element. The angle should preferably not exceed approximately 260° since the area in the element for receiving the finger will be more similar to an opening or bore rather than a recess. It is believed that for psychological reasons, individuals are frequently uncomfortable inserting a finger in an opening rather than placing the finger on an arcuate surface.

Thus, a novel fingerprint imaging apparatus has been disclosed. Although a prefered embodiment of the apparatus has been described in some detail, it is to be understood that various changes could be made by persons skilled in the art without departing from the spirit and scope of the subject invention as defined by the appended claims.

We claim:

1. A fingerprint imaging apparatus comprising:
   a frame;
   a carriage rotatably mounted on said frame;
   motor drive means for rotatably driving said carriage;
   a transparent optical element secured to said frame for receiving a finger to be imaged;
   a light source secured to said carriage which directs light towards said optical element; and
   a light detector secured to said carriage which receives light from said optical element, the position of said light detector being fixed with respect to said light source.

2. The imaging apparatus of claim 1 wherein said light detector includes a first mirror for receiving light from said optical element, a lens for focusing light from said first mirror, a second mirror for receiving light from said lens and a light sensitive element for receiving light from said second mirror.

3. The imaging apparatus of claim 2 wherein said light sensitive element is a photo-diode array.

4. The imaging apparatus of claim 3 wherein said diode array is a linear array.

5. The imaging apparatus of claim 1 wherein said optical element defines a recess for receiving the finger to be imaged.

6. The imaging apparatus of claim 5 wherein said optical element has a partial cylindrical cross-section which spans an angle of less than 260°.

7. The imaging apparatus of claim 1 wherein said motor drive means includes a motor and a motor control means for controlling said motor and wherein said motor control means causes said carriage to rotate between a carriage start position and a carriage stop position to perform an imaging scan.

8. The imaging apparatus of claim 7 wherein said motor control means also causes said carriage to return to a carriage home position intermediate said carriage start and stop positions upon completion of an imaging scan.

9. The imaging apparatus of claim 8 wherein said motor control means further includes finger detect means for detecting when a finger is present on said optical element.

* * * * *